United States Patent [19]

McClure et al.

[11] 4,060,565

[45] Nov. 29, 1977

[54] HYDROCARBON CONVERSION PROCESS USING A SUPPORTED PERFLUORINATED POLYMER CATALYST

[75] Inventors: James D. McClure; Stanley G. Brandenberger, both of Houston, Tex.

[73] Assignee: Shell Oil Company, Houston, Tex.

[21] Appl. No.: 783,917

[22] Filed: Apr. 1, 1977

Related U.S. Application Data

[62] Division of Ser. No. 663,956, March 4, 1976, Pat. No. 4,038,213.

[51] Int. Cl.$^2$ .............................................. C07C 3/54
[52] U.S. Cl. .......................... 260/671 C; 260/671 R
[58] Field of Search ....................... 260/671 R, 671 C

[56] References Cited

U.S. PATENT DOCUMENTS

| 3,326,866 | 6/1967 | Haag | 260/671 R |
|---|---|---|---|
| 3,336,410 | 8/1967 | Bloch et al. | 260/671 R |

OTHER PUBLICATIONS

Kapura et al., "Sulfonated Polymers as Alkylation Catalysts," Ind. Eng. Chem. Prod. Res. Develop, vol. 12, No. 1, 1973, pp. 62–67.

*Primary Examiner*—Herbert Levine
*Assistant Examiner*—C. E. Spresser
*Attorney, Agent, or Firm*—Dean F. Vance

[57] ABSTRACT

A process and catalyst for the conversion of hydrocarbons is disclosed. The catalyst is a supported solid perfluorinated polymer containing pendent sulfonic acid groups. The processes include alkylation of isoparaffins, isomerization of normal alkanes, disproportionation of toluene, and the alkylation of benzene.

6 Claims, No Drawings

HYDROCARBON CONVERSION PROCESS USING A SUPPORTED PERFLUORINATED POLYMER CATALYST

This is a division, of application Ser. No. 663,956, filed Mar. 4, 1976, now U.S. Pat. No. 4,038,213.

BACKGROUND OF THE INVENTION

Hydrocarbon conversion and the isomerization of hydrocarbons in particular, is of special importance to the petroleum industry. In recent years, with the advent of catalytic converters in automobiles and the required use of non-leaded gasoline, a need has arisen for higher octane number gasolines. Natural straight-run gasolines, i.e., naphthas, contain, chiefly, normal paraffins, such as normal pentane and normal hexane, which have relatively low octane numbers. It has become essential, therefore, to convert these low octane components to their higher octane counterparts. The isomerization of these hydrocarbon components accomplish this conversion, i.e., the isomers resulting have a much higher octane rating. Hence, the facility with which this isomerization is accomplished has become of prime importance.

Likewise, the need for isoparaffins, benzene, xylene, and ethyl benzene as building components in the petrochemical industry is increasing. Accordingly, the need for improved hydrocarbon conversion processes in the petrochemical industry is also great.

One of the primary hydrocarbon conversion processes now employed is the alkylation of isoparaffins. It was thought that certain sulfonated fluorocarbon polymers possess sufficient activity and stability to be useful as alkylation catalysts. However, in a recent study by Kapura and Gates, Sulfonated Polymers as Alkylation Catalysts, Industrial Engineering Chemistry Product Research Development, Vol. 12, No. 1, pp. 62–66 (1973), it was found that a sulfonated fluorocarbon vinyl ether polymer was inactive in alkylating isobutane with propylene in the gas phase and in a mole ratio of 5 to 1 at 260° C. The conclusion reached in that study was that the sulfonated fluorocarbon vinyl ether polymer catalyst was too weakly acidic to catalyze paraffin alkylation and that the polymer was not a useful catalyst. That study also showed that these same ion exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C." Contrary to the conclusions reached by Kapura and Gates, it has now been found that a supported perfluorinated polymer containing pendant sulfonic acid groups is a very active catalyst in the preparation of ethylbenzene from benzene and ethylene, in the alkylation of isoparaffins, in the isomerization of normal alkanes, and in the disproportionation of toluene.

SUMMARY OF THE INVENTION

The present invention comprises an improved hydrocarbon conversion process which comprises contacting said hydrocarbons under hydrocarbon converting conditions with a supported perfluorinated polymer catalyst containing a repeating structure selected from the group consisting of:

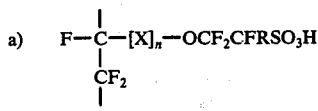

or

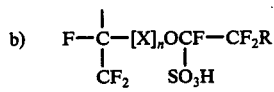

where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical.

Also disclosed is a novel catalyst composition for the conversion of hydrocarbons which comprises a catalytic component dispersed on a solid, porous support. The catalytic component is the perfluorinated polymer having the structure I or II above. The solid porous support has an effective pore diameter of between about 50 A and about 600 A and is preferably selected from the group consisting of alumina, silica, silica-alumina and porous glass.

DETAILED DESCRIPTION OF THE INVENTION

A. The Catalyst Composition

The catalyst employed in the present invention is a solid at reaction conditions. The catalyst broadly comprises a perfluorinated polymer having acid groups in the amount of about 0.01 to 5 mequiv/gram catalyst. Preferably, the polymer contains about 0.05 to 2 mequiv/gram of catalyst.

In a specific embodiment, the polymer catalyst contains a repeating structure selected from the group consisting of:

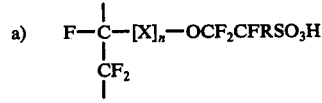

or

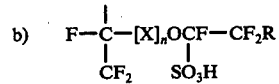

where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical. In a preferred embodiment, $n$ is 1 or 2, Y is a trifluoromethyl radical, R is fluorine, and m is 2. Catalysts of the above-noted structure typically have a molecular weight of between about 1,000 and 500,000 daltons.

Polymer catalysts of the above-noted structure can be prepared in various ways. One method, disclosed in Connolly et al, U.S. Pat. No. 3,282,875 and Cavanaugh et al, U.S. Pat. No. 3,882,093, comprises polymerizing vinyl compounds of the formula:

$$CF=CF[X]_nOCF_2CFRSO_3H \qquad \text{III}$$

or $$CF=CF[X]_nOCFCF_2R \atop \quad\quad\quad\quad\quad |\atop \quad\quad\quad\quad\quad SO_3H \qquad \text{IV}$$

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from $-50°$ to $+200°$ C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of structure III or IV with perfluoroethylene and/or perfluoro-alpha-olefins. A preferred copolymer prepared by polymerizing perfluoroethylene with a perfluorovinyl ether containing attached sulfonic acid groups would have the following structure:

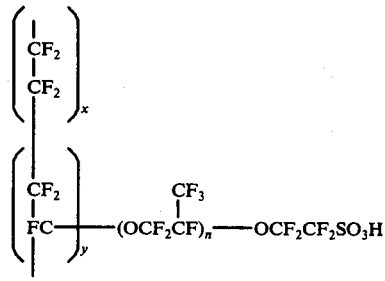

wherein i n = 1 or 2 and the ratio of $x$ over $y$ varies from about 2 to about 50. The polymer of structure V is available commercially under the tradename of NAFION ® resin. Catalysts of the above-noted structure V offer the advantages of high concentrations of accessible acid groups in a solid phase.

The catalyst of the present invention is supported on a porous solid inert support. The supported catalysts possess greater activity per unit of acid present than do the unsupported catalysts. By porous solid support is meant an inert support material having a porous structure and an average pore diameter of between about 50 A and about 600 A or higher. Preferably, the average pore diameter of the support is greater than about 200 A. The porous solid support of the subject invention is preferably selected from the inorganic oxide group consisting of alumina, fluorided alumina, zirconia, silica, silica-alumina, magnesia, chromia, boria, and mixtures and combinations thereof. Other porous solid supports may also be used such as bauxite, kieselguhr, kaolin, bentonite, diatomaceous earth and the like. Other porous solid supports such as polytetrafluoroethylene, carbon, e.g., charcoal, polytrichlorofluoroethylene, porous glass, and the like may also be used. Basically, the support should be substantially inert to the catalyst, and be insoluble in the mixture under reaction conditions.

The average pore diameter (also known as effective pore diameter) of the support, which is related to the ratio of pore volume to surface area, is an important consideration in the choice of support. Generally, as the average pore diameter of the support is increased, the activity of the catalyst is increased. For example, as shown in the Illustrative Embodiments which follow, an isomerization catalyst composition having a porous glass support with a 207 A average pore diameter was only about 60% as active as an isomerization catalyst composition having a porous glass support with a 310 A average pore diameter. Most preferably, the support should possess both a high surface area and a high average pore diameter.

The weight ratio of catalyst to support varies from about 0.1:100 to about 30:100, preferably from about 1:100 to about 15:100. The support is preferably impregnated with the catalyst by dissolving the catalyst in a solvent, such as ethanol, mixing the support and the catalyst solution, and then drying the impregnated support under vacuum at a temperature of between about 25° C and about 100° C so as to remove the solvent.

The invention is further defined with reference to a variety of particular hydrocarbon conversion processes.

B. Alkylation of Isoparaffins

The catalytic alkylation of paraffins involves the addition of an isoparaffin containing a tertiary hydrogen to an olefin. The process is extensively used by the petroleum industry to prepare highly branched paraffins mainly in the $C_7$ to $C_9$ range, which are high quality fuels for ignition engines. The overall process as to chemistry is a composite of complex reactions, and consequently a rigorous control of operating conditions and of catalyst is needed to assure predictable results.

Acid catalyzed hydrocarbon conversion processes comprising contacting an alkane with an olefin are well known. The reactants are generally contacted in the liquid phase and within a broad temperature range of about $-100°$ F to about 100° F with an acid catalyst such as, for example, sulfuric acid, fluorosulfuric acid or a halogen acid, such as hydrofluoric acid. Typical alkylation processes are disclosed in U.S. Pat. Nos. 2,313,103, 2,344,469, 3,864,423 and British Pat. No. 537,589. Catalyst moderators, such as water and lower monoethers as disclosed in U.S. Pat. No. 3,887,635, are often employed to improve the selectivity of the catalyst.

The catalysts employed in the above-noted references are liquid catalysts. Therefore, the process equipment must be necessarily complex. The reaction zone typically contains elaborate hardware to ensure intimate mixing of catalyst and reactions. In addition, a separation chamber is required to separate the catalyst from the hydrocarbon product. Further, since the reaction typically takes place at lower than ambient temperature, refrigeration facilities are also a necessary part of the process.

One means to improve the alkylation process would be to employ a solid catalyst instead of a liquid catalyst. However, conventional solid acid catalysts, such as zeolites, are not very stable in their catalytic activity. For example, during isobutane/butene-2 alkylation, zeolites undergo catastrophic decline in activity in 4 to 6 hours. Likewise, other solid alkylation catalysts, such as HF antimony pentafluoride catalyst as disclosed in U.S. Pat. No. 3,852,371, are not commercially stable catalysts.

In the present invention, a $C_4$ to $C_6$ isoparaffin containing a tertiary hydrocarbon or a hydrocarbon stream containing such isoparaffins is contacted with a $C_2$ to $C_5$ monoolefin, mixtures thereof, or hydrocarbon streams containing such olefins, in the liquid phase and at a temperature of between about 80° C and about 225° C in the presence of the catalyst composition of the instant invention.

The present invention has a distinct advantage over the typical alkylation process in that the catalyst is a solid catalyst thereby eliminating many of the mixing, settling, separation, and neutralization problems associated with catalysts such as sulfuric acid, hydrofluoric acid, or fluoromethane sulfuric acid. The present catalyst is also superior to the other solid catalysts such as zeolites in that the present catalyst is very stable under reaction conditions. For example, catalyst runs with the instant catalyst of over 200 hours have been achieved with no appreciable decline in catalyst activity.

Further, contrary to prior investigations, the present catalyst is very active in the alkylation reaction resulting in over 90% conversion of the olefin and over 80% $C_8$ selectivity. In addition, the trimethylpentane selectivity (basis $C_8H_{18}$) of the present catalyst is over 75%.

As shown in the Illustrative Embodiments which follow, the supported catalysts have a much greater activity than do the unsupported catalyst based on the number of grams of catalyst present. For example, the activity of a 1% NAFION ® resin on a Johns Mansville Chromosorb T is 2.5 times greater than a 5% Nafion resin on silica support and about 12 times greater than an unsupported Nafion resin catalyst per unit of actual catalyst present.

The olefin feed for the present invention contains olefins selected from the group consisting of $C_2$ to $C_5$ monoolefins and mixtures thereof. Examples of suitable olefins include propylene, isobutylene, butene-1, butene-2, trimethylethylene, the isomeric amylenes and mixtures thereof. In actual commercial use, however, these olefins will contain other hydrocarbons. The process of the instant invention contemplates the use of various refinery cuts as feedstocks. Thus, $C_3$, $C_4$ and/or $C_5$ olefin cuts from thermal and/or catalytic cracking units; field butanes which have been subjected to prior isomerization and partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present process.

The isoparaffin feed for the present invention comprises $C_4$ to $C_6$ isoparaffins containing tertiary hydrocarbon substituents, mixtures thereof, and hydrocarbon streams containing such components. A preferred isoparaffin is isobutane.

In order to prevent polymerization of the olefin, a large excess of isoparaffin is used. The weight ratio of isoparaffin to olefin varies from about 5:1 to about 1000:1, preferably about 20:1 to about 60:1. It has been found that when the isobutane to butene ratio is increased from 10:1 to 40:1, the $C_8$ selectivity and the total yield of greater than or equal to $C_5$ products are significantly increased while the yield of $C_{11}$–$C_{12}$ and $C_{14}$–$C_{16}$ products are decreased.

The process may be carried out either as a batch or continuous type of operation, although it is preferred to carry out the process continuously. It has been generally established that in alkylation processes, the more intimate the contact between the feedstock and the catalyst, the better the yield of saturated product obtained. With this in mind, the present process, when operated as a batch operation, is characterized by the use of vigorous mechanical stirring or shaking of the reactants and catalyst.

When employing a continuous process, the feedstreams may be contacted with the supported catalyst in any suitable reactor. In one embodiment, the supported catalyst is packed in a vertical, tubular reactor bed with inert supports, such as ceramic balls or silicon carbide, above and below the supported catalyst to prevent entrainment of the solid catalyst. In a further embodiment, the supported catalyst is mixed with an inert material, such as quartz, and loaded in the reactor so as to improve the fluid dynamics of the system. The flow of the reactant feed stream may be upflow or downflow, with an upflow arrangement being preferred to ensure liquid phase alkylation.

Reaction temperature is varied between about 80° C and about 225° C depending upon the type of products desired. The reaction temperature must be kept below about 225° C due to the lack of stability of the catalyst at temperatures of over 250° C. A preferred temperature range is between about 80° C and about 130° C. In general, the activity of the catalyst is greater at the higher temperatures. That is, as temperature increases, the conversion of olefin increases.

In general, the pressure in the alkylation reaction zone is maintained to keep the reactants in the liquid phase, and accordingly, will vary with the reactants employed and the reaction temperatures. Typical reaction zone pressure varies from about 10 psig to about 2,000 psig.

The weight hourly space velocity effectively measures the catalyst concentration employed, and hence also measures the relative activity of the catalyst. Weight hourly space velocity (WHSV) is defined as the weight per hour of olefin feed divided by the weight of catalyst (not including support) employed. For non-supported catalyst, the WHSV varies between about 0.05 and about 1.0, preferably about 0.15 and about 0.5. For a supported catalyst, the WHSV varies between about 0.5 to about 10.0. The larger WHSV employed for supported catalysts is possible because of the greater activity of the supported catalyst.

In a preferred embodiment, a gas stream is introduced into the reactor along with the olefin and isoparaffin feed streams. Typically, the gas is an inert gas such as nitrogen. However, it has been found that when the gas stream also contains hydrogen, the total yield of $C_5$ or greater products is increased without significantly increasing the n-butane selectivity or changing the trimethylpentane selectivity. The effect of including this gas stream in the alkylation reaction is to improve the percentage of $C_8H_{18}$ in the $C_8$ product, which improvement most likely occurs via hydride transfer from hydrogen to an intermediate $C_8$ carbonium ion to give a $C_8H_{18}$ alkane.

The reaction products obtained are highly branched paraffins, mainly in the $C_5$ to $C_{12}$ range. The butenes produce mainly $C_8$ hydrocarbons, principally dimethylhexanes and trimethylpentanes, while isobutylene results in mainly trimethylpentanes. It is not necessary to neutralize the reaction products of the present invention, since little, if any, of the sulfonic acid groups on the catalyst are removed during the reaction.

The principal use of the alkylate produced according to the present invention is in the blending of motor gasoline. Alkylate is a preferred gasoline blending component because of its high octane number, which number is enhanced by the presence of high concentrations of $C_8$ hydrocarbons. Trimethylpentane is a particularly valuable alkylate component.

The invention is further illustrated by means of the following Comparative Example and Illustrative Embodiments which are given for the purpose of illustration only, and the invention is not to be regarded as limited to any of the specific materials or conditions recited therein.

In the Comparative Example and Illustrative Embodiments, the reactor employed was a 17 inch stainless steel tube equipped with both a liquid feed upflow inlet and a nitrogen inlet. The catalyst bed occupied about 10 inches in the center of the reactor; and on either side of the catalyst bed were packed about 10 grams of carborundum chips. The catalyst bed was intitially charged with liquified isobutane at a flow rate of 10-20 milliliters per hour after the reactor was heated to 80°-120° C. Once the reactor was completely flooded with isobutane, the mixture of olefin and isoparaffin were charged to the reactor. In all cases, the olefin employed was 2-butene and the isoparaffin employed was isobutane.

In the Comparative Example and Illustrative Embodiments, the reactants were introduced in an upflow manner. Pressure in all cases was kept at 500 psig to maintain a liquid phase. In all cases, a 100% nitrogen gas was added at a rate of 0.3 liters per hour.

The products were recovered at periodic intervals and analyzed by gas chromatography. The percentage of alkenes in the $C_8$ fraction were determined by washing the fraction with 96% sulfuric acid to remove the alkenes.

In the Comparative Example and Illustrative Embodiments, the catalyst concentration is measured by weight hourly space velocity (WHSV, $hr^{-1}$) which is defined as the weight of the 2-butene feed per hour divided by the weight of catalyst employed. The weight of the support employed in the Illustrative Embodiments is not included in the calculation of WHSV. The total yield of greater than or equal to $C_5$ products is based on the weight of butene converted. Further, since 2,2,5-trimethyl-hexane is the only significant $C_9$ product formed and has a high octane number, it is included in the $C_8H_{18}$ fraction as reported.

COMPARATIVE EXAMPLE Ia

The catalyst for Comparative Example Ia was prepared by grinding Nafion XR granules with a blender to 150 micrometer or less particle size. The ground material was then treated twice with 30% sulfuric acid to convert the material from a potassium ($K^+$) form to the $H^+$ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

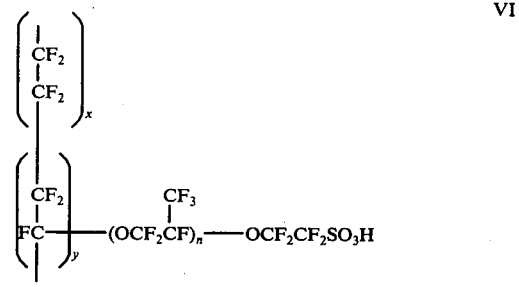

VI

In Comparative Example Ia, the catalyst bed comprised 2.5 grams of catalyst plus 7.5 grams of quartz particles. The isobutane to butene-2 ratio was maintained at about 10 to 1, whereas the WHSV and temperature were varied as indicated. The total length of the run lasted over 90 hours, and the results are presented below in Tables 1a, 2a and 3a.

Table 1a

| Time, hrs. | 3 | 5 | 7 | 9 | 11 | 13 | 15 | 16 | 18 | 19 | 20 | 22 |
|---|---|---|---|---|---|---|---|---|---|---|---|---|
| WHSV, hr | 0.4 | 0.4 | 0.4 | 0.4 | 0.4 | 0.66 | 0.66 | 0.66 | 0.66 | 0.66 | 0.66 | 0.66 |
| Temperature, ° C | 100 | 100 | 100 | 100 | 100 | 100 | 100 | 100 | 100 | 100 | 100 | 100 |
| Butene Conversion,% | 97 | 97 | 97 | 98 | 99 | 96 | 96 | 96 | 95 | 95 | 95 | 96 |
| Total Yield $\geq C_5$'s,%w | 150 | 147 | 146 | 146 | 147 | 145 | 146 | 146 | 146 | 146 | 145 | 146 |
| Products,%w | | | | | | | | | | | | |
| $C_5$-$C_7$ | 3 | 3 | 2 | 2 | 2.5 | 2 | 2 | 2 | 1.5 | 2 | 2 | 1.5 |
| $C_8$-$C_9$ | 65 | 65 | 65 | 65 | 64 | 68 | 68 | 70 | 71 | 70 | 71 | 71 |
| $C_{11}$-$C_{12}$ | 20 | 20 | 22 | 22 | 20 | 20 | 19 | 17 | 17 | 17 | 16 | 19 |
| $C_{14}$-$C_{16}$ | 12 | 12 | 11 | 11 | 13.5 | 10 | 11 | 11 | 11 | 11 | 11 | 9.5 |
| Composition of $C_8$,% | | | | | | | | | | | | |
| $C_8H_{18}$ | 81 | 70 | 70 | 70 | 73 | 66 | 67 | 65 | 65 | 65 | 64 | 64 |
| $C_8H_{16}$ | 19 | 30 | 30 | 30 | 27 | 34 | 33 | 35 | 35 | 35 | 36 | 36 |
| Composition of $C_8H_{18}$,% | | | | | | | | | | | | |
| Trimethylpentanes | 75 | 75 | 70 | 71 | 63 | 67 | 70 | 71 | 74 | 66 | 66 | 67 |
| Dimethylhexanes | 18 | 18 | 19 | 20 | 24 | 20 | 21 | 20 | 19 | 24 | 22 | 23 |
| Methylheptanes | 4 | 4 | 6 | 5 | 6 | 6 | 4 | 4 | 4 | 5 | 6 | 5 |
| 2,2,5-Trimethylhexane | 4 | 4 | 5 | 5 | 7 | 7 | 5 | 5 | 3 | 5 | 6 | 5 |

Table 2a

| Time, Hr. | 24 | 26 | 28 | 30 | 32 | 33 | 34 | 36 | 38 | 39.5 | 42.5 | 44.5 | 46 |
|---|---|---|---|---|---|---|---|---|---|---|---|---|---|
| WHSV, hr.$^{-1}$ | 0.66 | 0.66 | 0.66 | 0.66 | 0.66 | 0.66 | 0.66 | 0.66 | 0.66 | 0.66 | 0.66 | 0.66 | 0.66 |
| Temperature, °C | 90 | 90 | 90 | 90 | 90 | 90 | 90 | 90 | 90 | 90 | 90 | 90 | 90 |
| Butene, Conversion, % | 86 | 85 | 85 | 87 | 85 | 85 | 84 | 87 | 87 | 88 | 87 | 85 | 88 |
| Total Yield $\geq C_5$'s | 142 | 140 | 140 | 140 | 139 | 139 | 140 | 143 | 140 | 142 | 138 | 139 | 141 |
| Products, %w | | | | | | | | | | | | | |
| $C_5$-$C_7$ | 3 | 2 | 1 | 2 | 1 | 1 | 2 | 1 | 1 | 1 | 2 | 1 | 1 |
| $C_8$-$C_9$ | 74 | 74 | 73 | 74 | 73 | 74 | 73 | 74 | 74 | 75 | 74 | 73 | 74 |
| $C_{11}$-$C_{12}$ | 14 | 16 | 17 | 16 | 15 | 16 | 14 | 16 | 16 | 14 | 16 | 17 | 15 |
| $C_{14}$-$C_{16}$ | 10 | 9 | 9 | 9 | 11 | 9 | 11 | 9 | 9 | 10 | 8 | 9 | 10 |
| Composition of $C_8$, % | | | | | | | | | | | | | |
| $C_8H_{18}$ | 56 | 58 | 56 | 58 | 56 | 57 | 60 | 58 | 57 | 56 | 57 | 57 | 58 |
| $C_8H_{16}$ | 44 | 42 | 44 | 42 | 44 | 43 | 40 | 42 | 43 | 44 | 43 | 43 | 43 |
| Composition of $C_8H_{18}$, % | | | | | | | | | | | | | |
| Trimethylpentanes | 75 | 74 | 75 | 75 | 74 | 75 | 74 | 73 | 75 | 73 | 74 | 75 | 75 |
| Dimethylhexanes | 18 | 18 | 17 | 17 | 18 | 19 | 17 | 19 | 17 | 19 | 17 | 19 | 18 |
| Methylheptanes | 3 | 4 | 4 | 4 | 4 | 4 | 5 | 4 | 5 | 5 | 5 | 4 | 4 |
| 2,3,5-Trimethylhexane | 4 | 4 | 4 | 4 | 4 | 2 | 4 | 5 | 3 | 3 | 4 | 2 | 3 |

Table 3a

| Time, hrs. | 50 | 52 | 56 | 58 | 60 | 66 | 70 | 72 | 90 |
|---|---|---|---|---|---|---|---|---|---|
| Temperature, °C | 90 | 90 | 80 | 80 | 80 | 80 | 90 | 90 | 90 |
| WHSV, hr$^{-1}$ | 0.33 | 0.33 | 0.33 | 0.33 | 0.33 | 0.33 | 0.33 | 0.33 | 0.33 |
| Butene Conversion, % | 95 | 95 | 76 | 73 | 70 | 68–72 | 91 | 94 | 95 |
| Total Yield $\geq C_5$'s | | 140 | 139 | 138 | 138 | 138 | 140 | 141 | 141 |
| Products, %w | | | | | | | | | |
| $C_5$-$C_7$ | | 1.5 | <1 | <1 | <1 | <1 | 1 | 1.5 | 1.6 |
| $C_8$-$C_9$ | | 68 | 78 | 78 | 80 | 81 | 68 | 68 | 70 |
| $C_{11}$-$C_{12}$ | | 18 | 13 | 15 | 13 | 11 | 19 | 19 | 17 |
| $C_{14}$-$C_{16}$ | | 13 | 9 | 6 | 7 | 7 | 12 | 11.5 | 12 |
| Composition of $C_8$, % | | | | | | | | | |
| $C_8H_{18}$ | | 60 | 50 | 49 | 48 | 50 | 58 | 58 | 56 |
| $C_8H_{16}$ | | 40 | 50 | 51 | 52 | 50 | 42 | 42 | 44 |
| Composition of $C_8H_{18}$, % | | | | | | | | | |
| Trimethylpentanes | | 75 | 83 | 80 | 80 | 80 | 75 | 75 | 74 |
| Dimethylhexanes | | 18 | 12 | 14 | 14 | 15 | 19 | 18 | 17 |
| Methylheptanes | | 4 | 3 | 3 | 3 | 3 | 4 | 4 | 5 |
| 2,2,5-Trimethylhexane | | 3 | 2 | 3 | 3 | 2 | 2 | 3 | 4 |

ILLUSTRATIVE EMBODIMENT IA

The catalyst for Illustrative Embodiment Ia was prepared by impregnation of a silica gel support (Davison 57 with a 1.0 cc/g pore volume and 300 m²/g surface area) with an ethanol solution of Nafion XR granules. The ethanol was removed from the solid on a rotary evaporator leaving a 5% Nafion on silica catalyst. The structure of the resulting catalyst is exemplified by the repeating structure designated VI. About 5 grams of this catalyst was mixed with 5 grams of quartz to form the catalyst bed. The isobuane to butene-2 ratio was kept at 10:1 and the WHSV (based on the number of grams of Nafion resin present) was maintained at 3.3 hr$^{-1}$. The results along with the other operating conditions are presented below in Table 4a.

ILLUSTRATIVE EMBODIMENT IIA

The catalyst for Illustrative Embodiment IIa was 1.1% Nafion on a fluoropolymer support and was prepared by adding dropwise 5 grams of a 5.5% solution of Nafion XR granules in ethanol to 20 grams of Chromosorb T (Johns-Manville teflon 6) support. After the ethanol was removed and the catalyst dried, it was determined that the catalyst contained 1.1% Nafion. The catalyst bed for Illustrative Embodiment II comprised 10 grams of the catalyst with no quartz being added. The catalyst structure is similar to that employed in Illustrative Embodiment Ia.

The operating conditions were 110° C, isobutane to butene-2 ratio of 10:1, and a WHSV (based on the number of grams of Nafion resin present) of 8.2 hr$^{-1}$. The results are presented below in Table 5a.

Table 4a

| Time, Hrs | 2 | 4 | 6 | 7 | 22.5 | 25.5 | 30.5 | 46.5 | 47.5 |
|---|---|---|---|---|---|---|---|---|---|
| Temperature, °C | 100 | 100 | 100 | 100 | 110 | 110 | 110 | 110 | 110 |
| Butene Conv., % | 74 | 73 | 70 | 65 | 70 | 69 | 68 | 71 | 70 |
| Total Yield $C_5$'s | — | 137 | 139 | — | 138 | 137 | 138 | 138 | 138 |
| Products, %w | | | | | | | | | |
| $C_5$-$C_7$ | | 2 | 2 | | 1 | 2 | 1.5 | 1 | 1.5 |
| $C_8$-$C_9$ | | 72 | 76 | | 73 | 72 | 74 | 75 | 76 |
| $C_{11}$-$C_{12}$ | | 20 | 16 | | 17 | 17 | 17 | 17 | 15 |
| $C_{14}$-$C_{16}$ | | 6 | 6 | | 9 | 9 | 6 | 7 | 7 |
| Composition of $C_8$,% | | | | | | | | | |
| $C_8H_{18}$ | | 51.5 | 51 | | 52 | 51.5 | 51 | 50 | 51 |
| $C_8H_{16}$ | | 48.5 | 49 | | 48 | 48.5 | 49 | 50 | 49 |
| Composition of $C_8H_{18}$,% | | | | | | | | | |
| Trimethylpentanes | | 74 | 76 | | 70 | 72 | 74 | 72 | 77 |
| Dimethylhexanes | | 19 | 17 | | 18 | 21 | 19 | 21 | 17 |
| Methylheptanes | | 6 | 6 | | 8 | 6 | 6 | 6 | 5 |
| 2,2,5-Trimethylhexane | | 1 | 1 | | 4 | 1 | 1 | 1 | 1 |

Table 5a

| Time, hrs. | 4 | 20 | 24 | 28 | 44 | 48 | 52 | 68 | 74 |
|---|---|---|---|---|---|---|---|---|---|
| Butene Conv., % | 65 | 70 | 70 | 71 | 65 | 65 | 65 | 68 | 65 |
| Total Yield $C_5$'s | — | 138 | 138 | — | 137 | 137 | — | 137 | 137 |
| Products, %w | | | | | | | | | |
| $C_5$–$C_7$ | — | 2 | 1 | — | 1 | 1 | — | 1 | 1 |
| $C_8$–$C_9$ | — | 76 | 76 | — | 74 | 74 | — | 76 | 79 |
| $C_{11}$–$C_{12}$ | — | 16 | 14 | — | 17 | 17 | — | 14 | 14 |
| $C_{14}$–$C_{16}$ | — | 6 | 9 | — | 8 | 8 | — | 9 | 6 |
| Composition of $C_8$,% | | | | | | | | | |
| $C_8H_{18}$ | — | 50 | 50 | — | 50 | 49 | — | 49 | 48 |
| $C_8H_{16}$ | — | 50 | 50 | — | 50 | 51 | — | 51 | 52 |
| Composition of $C_8H_{18}$, % | | | | | | | | | |
| Trimethylpentanes | — | 80 | 80 | — | 80 | 80 | — | 80 | 80 |
| Dimethylhexanes | — | 14 | 15 | — | 15 | 14 | — | 15 | 15 |
| Methylheptanes | — | 5 | 4 | — | 4 | 5 | — | 4 | 4 |
| 2,2,5-Trimethylhexane | — | 1 | 1 | — | 1 | 1 | — | 1 | 1 |

C. ISOMERIZATION OF NORMAL ALKANES

Heretofore, it has been known that the isomerization of normal paraffins, particularly normal hexane, to their equilibrium mixtures of branched chain isomers, substantially increases the octane rating of the paraffinic hydrocarbons. In attempting to produce such equilibrium mixtures of isoparaffinic hydrocarbons, several catalytic processes have been developed. In one lower temperature process, isomerization is effected over an aluminum chloride catalyst. This process is costly to operate because of extensive corrosion effects caused by the acidic sludge formed from the aluminum chloride catalyst material, thereby requiring expensive alloy equipment. Moreover, moisture and high-molecular weight hydrocarbons usually present as contaminants in the charge stock cause deterioration of the catalyst and necessitate its frequent replacement. One higher temperature process utilizes a catalyst such as platinum on a silica-alumina base to promote hydroisomerization of normal paraffins in the presence of hydrogen at temperatures of the order of 700° to 800° F. At these high temperatures, the equilibrium mixture of isomers is such that substantial recycling of a portion of the paraffin feed is necessary to obtain the desired improvement in octane ratings.

There are numerous other catalyst systems useful in the isomerization of normal paraffins. These catalyst systems include hydrogen mordenite and platinum on alumina, U.S. Pat. No. 3,432,568; hydrofluoric acid-antimony pentafluoride, U.S. Pat. No. 3,903,196; zeolites, U.S. Pat. No. 3,770,845; and $SBF_5$-HF on a ruthenium-promoted fluorided alumina, U.S. Pat. No. 3,864,425.

In the present invention, a $C_4$ to $C_8$ normal paraffin feedstock is isomerized by contacting the feed at a temperature of between about 125° C and 225° C and a pressure of between about 0 psig and about 1,000 psig with the catalyst composition disclosed herein.

The catalysts of the present invention possess an improved activity, selectivity and stability over many of the known isomerization catalysts. In addition, the present catalysts, contrasting numerous other popular isomerization catalysts, are not extremely sensitive to water contamination. For example, a water concentration of about 100-150 parts per million in a normal hexane feed stream had no effect on a catalyst of the present invention. Further, as compared to a commercial platinum-on-mordenite isomerization catalyst, the catalyst employed in our invention can catalytically promote an isomerization reaction at a significantly lower temperature (75° C lower). At this lower temperature, not only is the conversion of normal paraffins to isoparaffins substantially increased, but the lower temperature also reduces the excess cracking often encountered at the higher temperatures employed with other catalysts.

The paraffin feed which can be isomerized according to the process of the present invention includes substantially pure normal paraffins having from 4 to 8 carbon atoms, mixtures of such normal paraffins, or hydrocarbon fractions rich in such normal paraffins. The paraffin feed may also contain other isomerizable paraffins such as cycloparaffins (sometimes referred to as napthenes). The most preferred feedstocks to the process of the present invention are a $C_5$ and/or $C_6$ normal paraffin feed. A particularly preferred feedstock is one containing predominantly (greater than 60% volume) normal hexane.

The stability of the present catalysts in isomerizing a normal paraffin feedstock is greatly improved by the addition of certain hydrocarbon catalyst stabilizers such as isobutane and benzene. When employing isobutane as a stabilizer, the volume ratio of isobutane present in the feed to normal paraffin in the feed should be between about 0.5:1 to about 2:1, preferably about 1:1. It has been found that a ratio of isobutane to normal hexane feed of about 1:1 results in a much improved catalyst stability and activity over a feedstock containing no isobutane. Further, it has been found that a 1:1 isobutane to normal hexane ratio gives better results than does either 0.5:1 or 2:1 ratio. When employing benzene as the catalyst stabilizer, the volume ratio of benzene to normal paraffin in the feed should be between about 0.002:1 and about 0.02:1, preferably between about 0.003:1 and about 0.01:1. It has been found that by increasing the benzene concentration in a normal nexane feed from about 0.25% to 0.5%, the activity of the catalyst is increased. A further increase to 1.0% benzene shows no advantage over 0.5% benzene.

Reaction temperature is varied between about 125° C and about 225° C, preferably between about 172° C and about 200° C. The reaction temperature must be kept below about 225° C due to the lack of stability of the catalyst at temperatures of over 250° C. In general, the activity of the catalyst is greater at the higher temperatures. That is, as the temperature increases, the conversion of normal paraffin increases.

In general, the pressure in the isomerization reaction zone is maintained at between about 0 psig and about 500 psig, preferably between about 50 psig and about 100 psig. The reaction may take place in either a gaseous phase or a liquid phase.

The process may be carried out either as a batch or continuous type of operation, although it is preferred to carry out the process continuously. When operated as a batch operation, the present process is characterized by the use of vigorous mechanical stirring or shaking of the reactants and catalyst. When employing a continuous process, the feed streams may be contacted with the catalyst in any suitable reactor. In one embodiment, the catalyst is packed in a vertical, tubular reactor bed with inert supports, such as ceramic balls or silicon carbide, above and below the catalyst to prevent entrainment of the solid catalyst. In a further embodiment, the catalyst is mixed with an inert material, such as quartz, and loaded in the reactor so as to improve the fluid dynamics of the system. The flow of the reactant feed stream may be upflow or downflow as desired.

The weight hourly space velocity effectively measures the catalyst concentration employed, and hence also measures the relative activity of the catalyst. Weight hourly space velocity (WHSV) is defined as the weight per hour of normal paraffin in the feed divided by the weight of catalyst (not including support) employed. For a non-supported catalyst, the WHSV varies from between about 0.05 hr$^{-1}$ and about 2.0 hr$^{-1}$, preferably about 0.4 hr$^{-1}$ and about 1.0 hr$^{-1}$. For a supported catalyst, the WHSV varies from between about 0.3 hr$^{-1}$ and about 10.0 hr$^{-1}$, preferably about 1.0 hr$^{-1}$ and about 4.0 hr$^{-1}$. The higher WHSV for the supported catalyst reflects the increased activity of the supported catalyst per unit of catalyst.

Hydrocarbon isomers produced from our process are useful as feedstocks for hydrocarbon alkylation processes. Further, they find utility as a gasoline blending stock because of their high antiknock properties.

The invention is further illustrated by means of the following Comparative Examples and Illustrative Embodiments which are given for the purpose of illustration only, and the invention is not to be regarded as limited to any of the specific materials or conditions recited therein.

In all examples and embodiments, the reactor employed was a 17-inch stainless steel tube equipped with a liquid feed downflow inlet. The catalyst bed occupied the central portion of the reactor, with several grams of carborundum chips on both sides of the catalyst bed to prevent entrainment of the catalyst.

In Comparative Examples Ib–IIIb and Illustrative Embodiments Ib to Xb, the hydrocarbon feed comprised normal hexane. The product from the reactor were analyzed by GLC.

COMPARATIVE EXAMPLE IB

The catalyst employed in Comparative Examples Ib and IIb was prepared by grinding Nafion XR granules with a blender to 150 micrometer or less particle size. The ground material was then treated twice with 30% sulfuric acid to convert the material from a potassium (K+)form to the H+ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or $2$ and the ratio of $x$ over $y$ varies from between 2 and about 50:

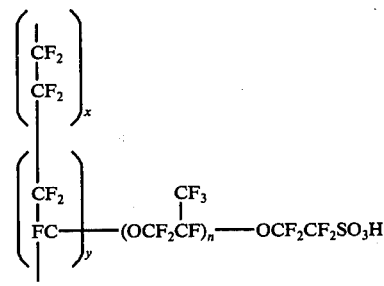

About 2.5 grams of the resulting polymer catalyst was mixed with 7.5 grams of quartz and loaded in the reactor. Reaction conditions were a pressure of 20 psig, weight hourly space velocity (define as the grams of hydrocarbon feed per hour divided by the grams of catalyst employed) of 0.9 hr$^{-1}$, and a reaction temperature of 175° C. The results are presented below in Table 1b.

Table 1b

| Time, Hr. | 1 | 2 | 3 | 4 | 5 | 6 | 7 |
|---|---|---|---|---|---|---|---|
| Composition of Product, %W | | | | | | | |
| $C_2$–$C_3$ | 3 | 2 | 1 | 0.8 | 0.6 | 0.4 | 0.2 |
| Isobutane | 14 | 11 | 9 | 8 | 5.5 | 3.5 | 2 |
| Isopentane + n-pentane | 22 | 18 | 15 | 13 | 10 | 8 | 5.7 |
| 3-Methylpentane | 8 | 7 | 7 | 5 | 4 | 3 | 1.5 |
| 2-Methylpentane | 13 | 12 | 11 | 9 | 7 | 4.5 | 3 |
| 2,3-Dimethylbutane | 5 | 4 | 4 | 3 | 2.5 | 1.5 | 1 |
| 2,2-Dimethylbutane | 8 | 7 | 6 | 5 | 4 | 2 | 0.5 |
| n-Hexane | 15 | 30 | 40 | 51 | 63 | 74 | 85 |
| $C_7$ Compounds | 10 | 8 | 6 | 4 | 3 | 2 | 1 |
| $\geq C_8$ Compounds | 2 | 1.5 | 1 | 1 | 0.5 | 0.2 | 0.1 |

COMPARATIVE EXAMPLE IIB

Comparative Example IIb was conducted in a similar manner to Comparative Example Ib except that the feed comprised a 1:1 volume ratio of isobutane to n-hexane. The pressure was maintained at 45–50 psig, and the WHSV (n-hexane feed only) at 0.47 hr$^{-1}$. The temperature was raised from 175° C to 200° C. after 54 hours. The results (on an iC$_4$ free basis) are presented below in Table 2b. After 54 hours, the unit was shut down over a weekend period.

Table 2b

| Time, Hrs. | 6 | 24 | 28 | 32 | 50 | 54 | 62 | 82 |
|---|---|---|---|---|---|---|---|---|
| Temperature, °C | 175 | 175 | 175 | 175 | 175 | 200 | 200 | 200 |
| Compositon of Product, %w (iC$_4$ free basis) | | | | | | | | |
| $C_2$–$C_3$ | 0.5 | 0.3 | 0.3 | 0.3 | 0.3 | 0.3 | 0.3 | 0.3 |
| Isopentane + n-pentane | 1.5 | 0.8 | 0.6 | 0.5 | 0.5 | 0.6 | 0.6 | 0.3 |
| 3-Methylpentane | 15 | 14 | 14 | 13 | 14 | 13 | 12 | 7 |
| 2-Methylpentane | 25 | 25 | 23 | 23 | 22 | 20 | 19 | 12 |
| 2,3-Dimethylbutane | 10 | 10 | 9 | 9 | 9 | 8 | 7 | 4 |
| 2,2-Dimethylbutane | 16 | 15 | 13 | 13 | 13 | 12 | 11 | 3 |
| n-Hexane | 30 | 34 | 39 | 40 | 41 | 45 | 50 | 73 |
| Methylcyclopentane | 0.2 | 0.05 | 0.05 | 0.05 | 0.05 | 0.05 | 0.03 | 0.02 |
| $C_7$ Compounds | 0.7 | 0.3 | 0.3 | 0.25 | 0.2 | 0.25 | 0.2 | 0.1 |
| $\geq C_8$ Compounds | 0.3 | 0.1 | 0.1 | 0.1 | 0.1 | 0.1 | 0.05 | 0.05 |

ILLUSTRATIVE EMBODIMENT Ib

Illustrative Embodiments Ib to Xb disclose the use of the catalyst of the present invention on various supports. In all cases, the supported catalyst was placed in a round-bottomed flask and a 5.5% solution of Nafion XR resin in ethanol was added dropwise. The resulting mixture was vigorously stirred with a mechanical stirrer during the impregnation, and stirring continued for 30 minutes thereafter. The ethanol was removed from the resulting supported catalyst by evaporation on a rotary evaporator at 25° C and 1 mm pressure for 2 hours and at 60° C and 1 mm pressure for an additional 4 hours. The dried, supported catalyst was then ground to a sufficient size so as to pass through a number 60 sieve. The resulting active catalyst structure is the same as that shown in Comparative Example Ib.

In Illustrative Embodiment Ib, the support employed was a high surface area silica having a 1.65 ml/g pore volume, 300 m²/g surface area and a 210 A average pore diameter. Nine grams of the resulting catalyst (6% catalyst on support) were loaded in the reactor. Reaction conditions were 20 psig pressure, 175° C temperature, and a WHSV of 3.0 hr$^{-1}$. Note that in all embodiments and claims, WHSV is measured on a support-free basis. The results are presented below in Table 3b.

Table 3b

| Time, Hrs. | 2 | 4 | 5 | 6 | 6.5 | 7.5 | 8.5 |
|---|---|---|---|---|---|---|---|
| Composition of Product, %w | | | | | | | |
| $C_2$–$C_3$ | 1.5 | 1.5 | 1.0 | 0.6 | 0.6 | 0.4 | 0.2 |
| Isobutane | 8 | 6 | 6 | 4 | 5 | 3 | 2 |
| Isopentane + n-pentane | 12 | 10 | 10 | 7 | 8 | 4 | 2 |
| 3-Methylpentane | 12 | 11 | 10 | 9 | 9 | 7 | 5 |
| 2-Methylpentane | 20 | 18 | 16 | 16 | 15 | 14 | 10 |
| 2,3-Dimethylbutane | 8 | 7 | 6 | 5 | 4 | 4 | 2 |
| 2,2-Dimethylbutane | 12 | 11 | 10 | 7 | 5 | 4 | 1 |
| n-Hexane | 20 | 30 | 37 | 42 | 50 | 62 | 77 |
| Methylcyclopentane | 0.2 | 0.2 | 0.2 | 0.1 | 0.1 | 0.1 | 0.05 |
| $C_7$ Compounds | 6 | 4 | 3 | 2 | 2 | 1 | 0.5 |
| $\geq C_8$ Compounds | 0.5 | 0.4 | 0.3 | 0.3 | 0.3 | 0.2 | 0.1 |

ILLUSTRATIVE EMBODIMENT IIb

An identical catalyst to that employed in Illustrative Embodiment Ib was employed in Illustrative Embodiment IIb. However, in Illustrative Embodiment Ib, the feed stream comprised isobutane and n-hexane in a 1:1 volume ratio. Reaction conditions included a 40–50 psig pressure and a WHSV of 2.2 hr$^{-1}$. The temperature was increased from 175° C to 200° C after 124 hours. Note that in all embodiments, WHSV is measured on basis of the n-hexane feed only, i.e., moderators such as isobutane or benzene are not included. The results are presented below in Table 4b.

Table 4b

| Time, Hours | 4 | 28 | 70 | 98 | 124 | 148 | 177 |
|---|---|---|---|---|---|---|---|
| Temperature, ° C | 175 | 175 | 175 | 175 | 175 | 200 | 200 |
| Composition of Product, %w (iC$_4$ free basis) | | | | | | | |
| $C_2$–$C_3$ | 0.5 | 0.3 | 0.3 | 0.3 | 0.2 | 0.5 | 0.2 |
| Isopentane + n-pentane | 2 | 0.6 | 0.5 | 0.4 | 0.4 | 0.6 | 0.3 |
| 3-Methylpentane | 12 | 12 | 12 | 12 | 12 | 13 | 7 |
| 2-Methylpentane | 20 | 20 | 20 | 20 | 20 | 21 | 13 |
| 2,3-Dimethylbutane | 8 | 8 | 8 | 8 | 8 | 8 | 4 |
| 2,2-Dimethylbutane | 12 | 12 | 11 | 12 | 12 | 16 | 4 |
| n-Hexane | 46 | 48 | 49 | 48 | 48 | 39 | 70 |
| Methylcyclopentane | 0.1 | 0.05 | 0.05 | 0.05 | 0.05 | 0.1 | 0.05 |
| $C_7$ Compounds | 0.3 | 0.2 | 0.2 | 0.2 | 0.2 | 0.3 | 0.1 |
| $\geq C_8$ Compounds | 0.1 | 0.1 | 0.05 | 0.05 | 0.05 | 0.1 | — |

ILLUSTRATIVE EMBODIMENT IIIb

Illustrative Embodiment IIIb was conducted in a similar manner to Illustrative Embodiment IIb except that the isobutane to n-hexane ratio was maintained at 0.5:1. Other operating conditions included a pressure of 40 psig, temperature of 175° C and a WHSV of 2.9 hr$^{-1}$. The results are presented below in Table 5b.

Table 5b

| Time, Hrs. | 4 | 22 | 27 | 46 | 51 | 70 |
|---|---|---|---|---|---|---|
| Composition of Product, %w (1C$_4$ free basis) | | | | | | |
| $C_2$–$C_3$ | 0.9 | 0.6 | 0.5 | 0.5 | 0.5 | 0.3 |
| Isopentane | 3 | 1.5 | 1.5 | 1.5 | 1.5 | 1.0 |
| 3-Methylpentane | 8 | 8 | 8 | 7 | 7 | 4 |
| 2-Methylpentane | 13 | 14 | 14 | 13 | 13 | 8 |
| 2,3-Dimethylbutane | 5 | 5 | 5 | 5 | 4 | 3 |
| 2,2-Dimethylbutane | 7 | 7.5 | 6 | 6 | 5 | 1.5 |
| n-Hexane | 62 | 63 | 64 | 66 | 68 | 82 |
| Methylcyclopentane | 0.1 | 0.1 | 0.1 | 0.1 | 0.05 | 0.05 |
| $C_7$ Compounds | 0.4 | 0.4 | 0.4 | 0.4 | 0.3 | 0.2 |
| $\geq C_8$ Compounds | 0.1 | 0.1 | 0.1 | 0.1 | 0.1 | 0.05 |

ILLUSTRATIVE EMBODIMENT IVb

Benzene acts as does isobutane in improving the selectivity and stability of the catalysts of the present invention. In Illustrative Embodiment IVb, an identical catalyst to that employed in Illustrative Embodiments Ib, IIb and IIIb was used. The normal hexane feed, however, contained 0.5% volume benzene and no isobutane. Other reaction conditions included a pressure of 20 psig, WHSV of 2.3 hr$^{-1}$, and a temperature of 175° C. The results are presented below in Table 6b.

Table 6b

| Time, Hrs. | 5 | 21 | 45 | 69 | 77 | 98 |
|---|---|---|---|---|---|---|
| Composition of Product, %w | | | | | | |
| $C_2$–$C_3$ | 0.2 | 0.2 | 0.4 | 0.3 | 0.1 | 0.05 |
| Isobutane | 0.3 | 0.3 | 0.3 | 0.3 | 0.2 | 0.1 |
| Isopentane + n-pentane | 0.4 | 0.4 | 0.3 | 0.3 | 0.3 | 0.1 |
| 3-Methylpentane | 12 | 12 | 12 | 12 | 10 | 4 |
| 2-Methylpentane | 20 | 20 | 20 | 20 | 18 | 8 |
| 2,3-Dimethylbutane | 8 | 8 | 8 | 8 | 7 | 2 |
| 2,2-Dimethylbutane | 11 | 12 | 11 | 12 | 10 | 2 |
| n-Hexane | 48 | 47 | 48 | 47 | 53 | 82 |
| Methylcyclopentane | 0.1 | 0.1 | 0.1 | 0.05 | 0.05 | 0.05 |
| $C_7$ Compounds | 0.2 | 0.2 | 0.2 | 0.2 | 0.2 | 0.05 |
| $\geq C_8$ Compounds | 0.05 | 0.05 | 0.05 | 0.05 | 0.05 | Trace |
| Benzene | 0.3 | 0.4 | 0.45 | 0.4 | 0.45 | 0.45 |

ILLUSTRATIVE EMBODIMENT Vb

Illustrative Embodiment Vb differs from Illustrative Embodiment IVb only in that the pressure was maintained at 18 psig, and the percentage of benzene in the normal hexane feed was reduced to 0.25% volume. The results are presented below in Table 7b.

Table 7b

| Time, Hrs. | 4 | 24 | 46 | 70 | 78 | 97 |
|---|---|---|---|---|---|---|
| Composition of Product, %w | | | | | | |
| $C_2$-$C_3$ | 0.2 | 0.2 | 0.2 | 0.2 | 0.2 | 0.1 |
| Isobutane | 0.5 | 0.5 | 0.5 | 0.5 | 0.5 | 0.3 |
| Isopentane + n-pentane | 0.7 | 0.7 | 0.6 | 0.7 | 0.7 | 0.3 |
| 3-Methylpentane | 10 | 8 | 9 | 8 | 7 | 4 |
| 2-Methylpentane | 17 | 16 | 15 | 15 | 13 | 7 |
| 2,3-Dimethylbutane | 6.5 | 6 | 6 | 6 | 5 | 2 |
| 2,2-Dimethylbutane | 9 | 8 | 8 | 7 | 6 | 1.5 |
| n-Hexane | 56 | 59 | 59 | 62 | 67 | 85 |
| Methylcyclopentane | 0.1 | 0.1 | 0.1 | 0.1 | 0.1 | 0.05 |
| $C_7$ Compounds | 0.3 | 0.3 | 0.3 | 0.3 | 0.3 | 0.2 |
| $\geq C_8$ Compounds | 0.1 | 0.1 | 0.1 | 0.1 | 0.1 | 0.05 |
| Benzene | 0.1 | 0.15 | 0.15 | 0.1 | 0.1 | 0.15 |

ILLUSTRATIVE EMBODIMENT VIb

The only change from Illustrative Embodiment Vb is that in Illustrative Embodiment VIb, the benzene concentration in the n-hexane feed is increased to 1.0% volume. The results are found below in Table 8b.

Table 8b

| Time, Hrs. | 4 | 23 | 28 | 47 | 52 | 71 |
|---|---|---|---|---|---|---|
| Composition of Product, %w | | | | | | |
| $C_2$-$C_3$ | 0.1 | 0.1 | 0.1 | 0.1 | 0.1 | 0.05 |
| Isobutane | 0.2 | 0.2 | 0.2 | 0.2 | 0.2 | 0.1 |
| Isopentane | 0.3 | 0.2 | 0.2 | 0.2 | 0.2 | 0.1 |
| 3-Methylpentane | 9 | 8 | 8 | 8 | 7 | 4 |
| 2-Methylpentane | 15 | 15 | 15 | 14 | 13 | 6 |
| 2,3-Dimethylbutane | 6 | 5 | 5 | 5 | 4.5 | 2 |
| 2,2-Dimethylbutane | 7 | 6 | 6 | 6 | 5 | 1.5 |
| n-Hexane | 61 | 64 | 64 | 65 | 68 | 85 |
| Methylcyclopentane | 0.1 | 0.1 | 0.1 | 0.1 | 0.05 | 0.05 |
| $C_7$ Compounds | 0.1 | 0.1 | 0.1 | 0.1 | 0.1 | 0.1 |
| $\geq C_8$ Compounds | 0.05 | 0.05 | Trace | Trace | Trace | — |
| Benzene | 0.6 | 0.9 | 0.8 | 0.90 | 0.90 | 0.90 |

ILLUSTRATIVE EMBODIMENT VIIb

In Illustrative Embodiment VIIb, the catalyst of the present invention was supported on a silica-alumina base (MSA-3) having a 1.0 ml/g pore volume, 510 m²/g surface area, and an 80 A average pore diameter. About 12 grams of the resulting inpregnated catalyst having a catalyst to support weight ratio of 4.5:100 was loaded in the reactor. Operating conditions included 40 psig pressure, 175° C temperature, WHSV of 2.12 hr$^{-1}$, and an isobutane to n-hexane feed ratio of 1:1. The results are presented below in Table 9b.

Table 9b

| Time, Hrs. | 4 | 20 | 25 | 28 | 44 | 50 |
|---|---|---|---|---|---|---|
| Composition of Product, %w (iC$_4$ free basis) | | | | | | |
| $C_2$-$C_3$ | 1 | 0.4 | 0.2 | 0.2 | 0.3 | 0.2 |
| Isopentane | 2 | 0.5 | 0.4 | 0.4 | 0.3 | 0.12 |
| 3-Methylpentane | 7 | 7 | 7 | 6 | 6 | 5 |
| 2-Methylpentane | 11 | 11 | 10 | 10 | 10 | 8 |
| 2,3-Dimethylbutane | 4 | 4 | 3 | 3 | 3 | 2 |
| 2,2-Dimethylbutane | 4 | 4 | 4 | 3 | 3 | 1.5 |
| n-Hexane | 71 | 73 | 75 | 77 | 77 | 83 |
| Methylcyclopentane | 0.1 | 0.05 | 0.05 | 0.05 | 0.05 | 0.05 |
| $C_7$ Compounds | 0.3 | 0.2 | 0.2 | 0.2 | 0.2 | 0.11 |
| $\geq C_8$ Comounds | 0.1 | 0.05 | 0.05 | 0.05 | 0.05 | 0.05 |

ILLUSTRATIVE EMBODIMENT VIIIb

In Illustrative Embodiment VIIIb, the support was a porous glass (98% SiO$_2$ and 2% B$_2$O$_3$) having a pore volume of 1.2 ml/g, surface area of 154 m²/g, and an average pore diameter of 310 A. The impregnated catalyst had a catalyst to support weight ratio of 5:100. About 4.5 grams of the supported catalyst was loaded in the reactor. Reaction conditions were a 40 psig pressure, WHSV of 5.3 hr$^{-1}$, 175° C temperature, and an isobutane to n-hexane ratio of 1:1. The results are presented below in Table 10b.

Table 10b

| Time, Hrs. | 2 | 23 | 45 | 53 | 77 | 98 |
|---|---|---|---|---|---|---|
| Composition of Product, %w (iC$_4$ free basis) | | | | | | |
| $C_2$-$C_3$ | 0.3 | 0.3 | 0.4 | 0.4 | 0.3 | 0.3 |
| Isopentane + n-pentane | 3.0 | 1.0 | 1.1 | 1.0 | 0.9 | 0.9 |
| 3-Methylpentane | 15 | 15 | 15 | 14.5 | 15 | 14.5 |
| 2-Methylpentane | 25 | 25 | 25 | 25 | 25 | 25 |
| 2,3-Dimethylbutane | 10 | 10 | 10 | 9.5 | 10 | 9.5 |
| 2,2-Dimethylbutane | 16 | 16 | 16 | 16 | 15 | 15 |
| n-Hexane | 30 | 32 | 32 | 33 | 33 | 34 |
| Methylcyclopentane | 0.1 | 0.1 | 0.1 | 0.1 | 0.1 | 0.1 |
| $C_7$ Compounds | 0.5 | 0.3 | 0.3 | 0.3 | 0.3 | 0.3 |
| $\geq C_8$ Compounds | 0.2 | 0.1 | 0.1 | 0.1 | 0.1 | 0.1 |

ILLUSTRATIVE EMBODIMENT IXb

In Illustrative Embodiment IXb, the support employed was a porous glass having a pore volume of 1.5 ml/g, surface area of 292 m²/g, and an average pore diameter of 207 A. The catalyst to support ratio was 4.5:100, and 4.5 grams of supported catalyst were employed. Reaction conditions included 40 psig pressure, WHSV of 4.4 hr$^{-1}$, temperature of 175° C, and an isobutane to n-hexane ration of 1:1. The results are presented below in Table 11b.

Table 11b

| Time, Hrs. | 2 | 21 | 26 | 47 | 53 | 74 |
|---|---|---|---|---|---|---|
| Composition of Product, %w (iC$_4$ free basis) | | | | | | |
| $C_2$-$C_3$ | 0.3 | 0.3 | 0.3 | 0.2 | 0.2 | 0.2 |
| Isopentane + n-pentane | 2.0 | 0.6 | 0.6 | 0.6 | 0.6 | 0.6 |
| 3-Methylpentane | 12 | 12 | 12 | 12 | 12 | 12 |
| 2-Methylpentane | 20 | 20 | 20 | 20 | 20 | 20 |
| 2,3-Dimethylbutane | 8 | 8 | 8 | 8 | 8 | 7 |
| 2,2-Dimethylbutane | 12 | 12 | 11 | 11 | 12 | 11 |
| n-Hexane | 45 | 47 | 48 | 48 | 47 | 49 |
| Methylcyclopentane | 0.1 | 0.1 | 0.1 | 0.1 | 0.1 | 0.1 |
| $C_7$ Compounds | 0.4 | 0.3 | 0.3 | 0.3 | 0.3 | 0.3 |
| $\geq C_8$ Compounds | 0.1 | 0.1 | 0.1 | 0.1 | 0.1 | 0.1 |

ILLUSTRATIVE EMBODIMENT Xb

In Illustrative Embodiment Xb, the support employed was a Pechiney alumina having a pore volume of 0.55 ml/g, surface area of 60 m²/g, and an effective pore diameter of 370 A. Catalyst to support ratio was 2.8:100. About 12 grams of the supported catalyst were loaded in the reactor. Reaction conditions included a 40 psig pressure, 175° C temperature, WHSV of 3.5 hr$^{-1}$, and an isobutane to n-hexane feed ratio of 1:1. The results are presented below in Table 12b.

Table 12b

| Time, Hrs. | 5 | 26 | 50 | 71 | 77 | 96 |
|---|---|---|---|---|---|---|
| Composition of Product, %w (iC$_4$ free basis) | | | | | | |
| $C_2$-$C_3$ | 0.3 | 0.3 | 0.2 | 0.2 | 0.2 | 0.2 |
| Isopentane | 1.0 | 0.8 | 0.8 | 0.8 | 0.8 | 0.5 |
| 3-Methylpentane | 15 | 15 | 15 | 15 | 15 | 10 |
| 2-Methylpentane | 25 | 25 | 25 | 24.5 | 25 | 17 |
| 2,3-Dimethylbutane | 10 | 10 | 10 | 9.5 | 9.5 | 6.5 |
| 2,2-Dimethylbutane | 15 | 15 | 15 | 14.5 | 14.5 | 9 |
| n-Hexane | 33 | 33 | 33 | 34.5 | 34.5 | 56.5 |
| Methylcyclopentane | 0.1 | 0.1 | 0.1 | 0.1 | 0.1 | 0.1 |
| $C_7$ Compounds | 0.3 | 0.3 | 0.3 | 0.3 | 0.3 | 0.2 |
| $\geq C_8$ Compounds | 0.1 | 0.1 | 0.1 | 0.1 | 0.1 | 0.05 |

ILLUSTRATIVE EMBODIMENT XIb

In Illustrative Embodiment XIb, the support was a low pore diameter CCI alumina having a pore volume of 0.85 ml/g, a surface area of 250 m²/g, and an effective pore diameter of 136 A. Catalyst to support ratio was about 3.7:100, and about 15 grams of supported catalyst were loaded in the reactor. Reaction conditions included a pressure of 40 psig, temperature of 175° C, WHSV of 2.2 hr$^{-1}$, and an isobutane to n-hexane ratio of 1:1. The results are presented below in Table 13b.

Table 13b

| Time, Hrs. | 2 | 23 | 44 | 66 | 74 | 95 | 100 |
|---|---|---|---|---|---|---|---|
| Composition of Product, %w (iC$_4$ free basis) | | | | | | | |
| C$_2$-C$_3$ | 0.5 | 0.2 | 0.2 | 0.2 | 0.3 | 0.1 | 0.1 |
| Isopentane | 3 | 0.4 | 0.4 | 0.4 | 0.5 | 0.2 | 0.2 |
| 3-Methylpentane | 13 | 12 | 12 | 12 | 12 | 4 | 2 |
| 2-Methylpentane | 21 | 20 | 20 | 20 | 20 | 8 | 4 |
| 2,3-Dimethylbutane | 8 | 8 | 8 | 8 | 8 | 2 | 1 |
| 2,2-Dimethylbutane | 13 | 12 | 12 | 12 | 12 | 2 | 1 |
| n-Hexane | 40 | 48 | 48 | 48 | 48 | 83 | 91 |
| Methylcyclopentane | 0.1 | 0.1 | 0.05 | 0.05 | 0.05 | 0.05 | 0.05 |
| C$_7$ Compounds | 0.3 | 0.2 | 0.2 | 0.2 | 0.2 | 0.1 | 0.1 |
| ≧C$_8$ Compounds | 0.1 | 0.05 | 0.05 | 0.05 | 0.05 | Trace | — |

COMPARATIVE EXAMPLE IIIb

Comparative Example IIIb was run with an identical catalyst and loading as that employed in Comparative Example IIb. However, in Comparative Example IIIb, the feed comprised n-pentane instead of n-hexane. Other operating conditions included a 45 psig pressure, WHSV of 0.45 hr$^{-1}$, and an isobutane to n-pentane ratio of 1:1. The temperature was increased from 175° C to 200° C after 30 hours. Results are presented below in Table 14b.

Table 14b

| Time, Hrs. | 5 | 26 | 32 | 52 | 60 | 82 | 84 |
|---|---|---|---|---|---|---|---|
| Temperature, ° C | 175 | 175 | 200 | 200 | 200 | 200 | 200 |
| Composition of Product, %w (iC$_4$ free basis) | | | | | | | |
| C$_2$-C$_3$ | 0.2 | 0.2 | 0.2 | 0.2 | 0.2 | 0.1 | 0.1 |
| Isopentane | 25 | 25 | 30 | 32 | 30 | 15 | 12 |
| n-pentane | 75 | 75 | 70 | 68 | 70 | 85 | 88 |
| C$_6$ Compounds | 0.1 | 0.2 | 0.2 | 0.2 | 0.2 | 0.1 | 0.1 |
| ≧C$_7$ Compounds | 0.05 | 0.05 | 0.5 | 0.05 | 0.05 | 0.05 | 0.05 |

D. Preparation of Ethylbenzene

As is well known to those skilled in the art, ethylbenzene is a desirable article of commerce since it is the starting material for the production of styrene. Generally, styrene is produced through the steam dehydrogenation of ethylbenzene. Ethylbenzene does occur, to some extend, in petroleum fractions and may be obtained from such fractions through the technique of super-distillation. However, the demand for styrene in recent times has far surpassed the availability of naturally occurring ethylbenzene. Accordingly, the prior art has resorted more and more to the alkylation of benzene with ethylene using various types of catalyst. Among the catalysts employed in the prior art are aluminum chloride, U.S. Pat. No. 3,848,012; phosphoric acid, U.S. Pat. No. 3,478,119; boron trifluoride-modified alumina, British Pat. No. 905,051; silica-alumina, U.S. Pat. No. 2,419,796; and zeolites, U.S. Pat. No. 3,751,504.

It is also known that certain sulfonated fluorocarbon vinyl ether polymers are useful in the alkylation of benzene with propylene in the vapor phase to form cumene. See the recent study by Kapura and Gates, supra. However, the conclusion reached by Kapura and Gates in their study was that the sulfonated polymer was not "a practically useful catalyst at temperatures greater than about 150° C". Contrary to the conclusions reached by Kapura and Gates for employing sulfonated polymers to prepare cumene from benzene and propylene, it has now been found that catalysts of the instant invention are very active in the preparation of ethylbenzene from benzene and ethylene. This finding is especially suprising since it is well known that propylene is more reactive than ethylene.

In the present invention, ethylene is reacted with benzene in the liquid phase over the present catalyst compositon and at a temperature of between about 125° C and 225° C. The catalysts and process of the present invention produce an ethylbenzene product containing very little (less than 0.1%) cumene, and with a relatively high percentage of ethylbenzene in the reaction zone effluent.

The ethylene feed stream suitable for use in the practice of the present invention may be either of high purity or of a lower purity. High purity ethylene streams comprise at least 90 mol percent ethylene, preferably over about 95 mol percent ethylene. However, it is often useful to employ lower purity ethylene streams. Preferred ethylene streams contain between about 35 and about 75 percent ethylene, usually less than about 50 percent ethylene, with the balance of the stream being largely inert gases such as ethane, methane and hydrogen. However, with either high or low purity ethylene, the ethylene feed stream should be substantially free from aromatics, acetylene, and other olefins.

The benzene to be used in the present invention should be of relatively high purity. However, the benzene is typically obtained from storage facilities and, therefore, will often be saturated with water. Contrary to the detrimental effect of water on the commercially used aluminum chloride and silica-alumina catalysts, water levels of as high as 100 ppm have no detrimental effect on the catalysts of the present invention.

In order to prevent polymerization of the ethylene, an excess of benzene is used. The mole ratio of benzene to ethylene varies from about 1.5:1 to about 10:1, preferably about 2:1 to about 5:1.

The process may be carried out either as a batch or continuous type of operation, although it is preferred to carry out the process continuously. It has been generally established that the more intimate the contact between the feedstock and the catalyst, the better the yield of desired product obtained. With this in mind, the present process, when operated as a batch operation, is characterized by the use of vigorous mechanical stirring or shaking of the reactants and catalyst.

When employing a continuous process, the feed streams may be contacted with the catalyst in any suitable reactor. In one embodiment, the catalyst is packed in a vertical, tubular reactor bed with inert supports, such as ceramic balls or silicon carbide, above and below the catalyst. The catalyst can be mixed with an inert material, such as quartz, and loaded in the reactor so as to improve the fluid dynamics of the system. The flow of the reactant feed stream may be upflow or downflow, with an upflow arrangement being preferred to ensure liquid phase alkylation.

Reaction temperature is varied between about 125° C and about 225° C. The reaction temperature must be kept below about 225° C due to the lack of stability of the catalyst at temperatures of over 250° C. A preferred temperature range is between about 150° C and about 210° C. In general, the activity of the catalyst is greater at the higher temperatures. That is, as temperature increases, the conversion of ethylene increases.

In general, the pressure in the reaction zone is maintained to keep the reactants in the liquid phase, and accordingly, will vary with the particular reactants employed and the reaction temperatures. Typical reaction zone pressure varies from about 10 psig to about 2,000 psig.

The weight hourly space velocity effectively, measures the catalyst concentration employed, and hence, also measures the relative activity of the catalyst. Weight hourly space velocity (WHSV) is defined as the weight per hour of total combined feed (benzene plus ethylene) divided by the weight of catalyst (including support) employed. For a supported catalyst, the WHSV varies between about 0.5 hr$^{-1}$ and about 20 hr$^{-1}$, preferably about 2 hr$^{-1}$ and about 10 hr$^{-1}$.

The invention is further illustrated by means of the following Comparative Example and Illustrative Embodiments which are given for the purpose of illustration only, and the invention is not to be regarded as limited to any of the specific materials or conditions recited therein.

In Comparative Example Ic and Illustrative Emodiments Ic to IVc, the reactor employed was a 17-inch stainless steel tube equipped with a liquid feed upflow inlet. The catalyst bed occupied the central portion of the reactor, with several grams of carborundum chips on both sides of the catalyst bed to prevent entrainment of the catalyst. All reactions took place in the liquid phase.

COMPARATIVE EXAMPLE Ic

The catalyst employed in Comparative Example Ic was prepared by grinding Nafion XR granules with a blender to 150 micrometer or less particle size. The ground material was then treated twice with 30% sulfuric acid to convert the material from a potassium (K+) form to the H+ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

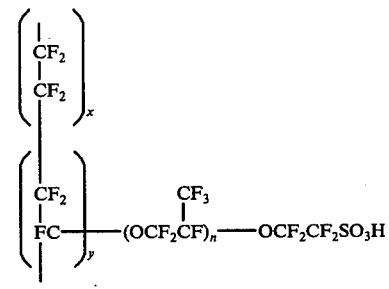

About 4.0 grams of the resulting olymer catalyst was mixed with 5.0 grams of quartz and loaded in the reactor. Reaction conditions were a pressure of 500 psig, a temperature of 175° C and an approximate benzene/ethylene mole ratio of 5:1. The weight hourly space velocity, WHSV (defined as the grams of total feed per hour divided by the grams of catalyst — including support — employed), varied from 1.0 hr$^{-1}$ to 8.0 hr$^{-1}$ as indicated in the results presented below in Table 1c.

Table 1c

| Time, hours | 4 | 24 | 44 | 50 | 74 | 78 |
|---|---|---|---|---|---|---|
| Temperature, ° C | 175 | 175 | 175 | 175 | 176 | 175 |
| WHSV | 1.0 | 1.0 | 1.0 | 2.0 | 4.0 | 8.0 |
| Ethylene Conversion, % | 100 | 100 | 100 | 100 | 100 | 100 |
| Ethylbenzene, %w in product | 15.6 | 15.4 | 15.5 | 16.3 | 16.9 | 17.5 |
| Selectivity, %w | | | | | | |
| Ethylbenzene | 80 | 80 | 80 | 84 | 86 | 88 |
| Butylbenzene | 1 | 1 | 1 | 1 | 1 | 1 |
| Diethylbenzene | 15 | 15 | 14.5 | 12.5 | 11 | 10 |
| Triethylbenzene | 3.6 | 3.1 | 3.5 | 2.1 | 1.8 | 1.5 |
| Tetraethylbenzene | 1.0 | 1.0 | 1.0 | 0.5 | 0.3 | — |

ILLUSTRATIVE EMBODIMENT Ic

Illustrative Emodiments Ic to IVc disclose the use of the catalyst of the present invention on various supports. In all cases, the supported catalyst was prepared by placing the support in a round-bottomed flask and adding, dropwise, a 5.5% solution of Nafion XR resin in ethanol. The resulting mixture was vigorously stirred with a mechanical stirrer during the impregnation, and stirring continued for 30 minutes thereafter. The ethanol was removed from the resulting supported catalyst by evaporation on a rotary evaporator at 25° C and 1 mm pressure for two hours and at 60° C and 1 mm pressure for an additional four hours. The dried, supported catalyst was then grond to a sufficient size so as to pass through a number 60 sieve. The resulting active catalyst structure is the same as that shown in Comparative Example Ic.

In Illustrative Embodiment Ic, the support employed was a high surface area silica having a 1.65 ml/g pore volume, 300 m$^2$/g surface area and a 210 A average pore diameter. Ten grams of the resulting catalyst (6% catalyst on support) were loaded in the reactor. Reaction conditions were 500 psig pressure and a benzene to ethylene ratio of about 5:1. WHSV and temperature were changed as indicated with the results below in Table 2c. Note that in all embodiments and claims, WHSV is measured on the total catalyst employed including the support.

Table 2c

| Time, hours | 18 | 23.5 | 46.5 | 50.5 | 70.5 | 77 |
|---|---|---|---|---|---|---|
| Temperature, ° C | 175 | 175 | 175 | 185 | 185 | 195 |
| WHSV | 0.5 | 0.9 | 0.9 | 1.8 | 3.6 | 3.6 |
| Ethylene Conversion, % | 100 | 100 | 100 | 99 | 90 | 98 |
| Ethylbenzene, %w in product | 16.2 | 16.7 | 16.9 | 17.4 | 16.1 | 17.8 |
| Selectivity, %w | | | | | | |
| Ethylbenzene | 86 | 88 | 89 | 91 | 93 | 93 |
| Butylbenzene | 1.6 | 1.5 | 1.3 | 1.0 | 0.8 | 0.6 |
| Diethylbenzene | 11 | 9.5 | 9.0 | 8.0 | 6.0 | 6.5 |
| Triethylbenzene | 1.0 | 1.0 | 0.8 | 0.4 | 0.2 | 0.2 |

ILLUSTRATIVE EMBODIMENT IIc

An identical catalyst to that employed in Illustrative Embodiment Ic was employed in Illustrative Embodiment IIc. However, in Illustrative Embodiment IIc, the reactor was charged with 4.5 grams of the supported catalyst and 4.5 grams of quartz; the benzene to ethylene mole ratio was decreased to about 3:1; and the WHSV was maintained at about 3.0 hr$^{-1}$. The temperature was varied as indicated in Table 3c below.

Table 3c

| Time, hours | 4 | 20 | 28 | 51.5 | 117 | 123 | 169 | 189 |
|---|---|---|---|---|---|---|---|---|
| Temperature ° C | 193 | 193 | 193 | 195 | 197 | 199 | 215 | 220 |
| Ethylene Conversion, % | 98 | 98 | 98 | 99 | 96 | 100 | 66 | 20 |
| Ethylbenzene %w product | 28.5 | 28 | 28.5 | 28.8 | 28 | 28 | 13.4 | 8.8 |
| Selectivity, %w | | | | | | | | |
| Ethylbenzene | 88 | 87 | 87 | 85 | 87 | 85 | 89 | 91 |
| Butylbenzene | 1.0 | 1.2 | 1.3 | 1.3 | 1.3 | 1.2 | 1.1 | 1.0 |
| Diethylbenzene | 9 | 9 | 9 | 11 | 9 | 11 | 9 | 8 |
| Triethylbenzene | 2 | 2 | 2 | 2.2 | 2 | 2.1 | 1.1 | 0.2 |
| Tetraethylbenzene | 0.6 | 0.6 | 0.6 | 0.6 | 0.6 | 0.6 | — | — |

ILLUSTRATIVE EMBODIMENT IIIc

In Illustrative Embodiment IIIc, the support was a porous glass (98% SiO$_2$ and 2% B$_2$O$_3$) having a pore volume of 1.2 ml/g, surface area of 154 m$^2$/g, and an average pore diameter of 310 A. The impregnated catalyst had a catalyst to support weight ratio of 5:100. About 4.5 grams of supported catalyst was loaded in the reactor along with 4.5 grams of quartz. Reactor pressure was maintained at 750 psig, WHSV at 3.0, and the benzene to ethylene ratio at 3:1. The results are presented below in Table 4c.

Table 4c

| Time, hours | 3 | 22 | 46 | 51 | 75 | 97 |
|---|---|---|---|---|---|---|
| Temperaure, ° C | 188 | 188 | 188 | 195 | 200 | 201 |
| Ethylene Conversion, % | 95 | 99 | 95 | 100 | 100 | 99 |
| Ethylbenzene, %w in product | 27.6 | 28.7 | 27.6 | 29 | 29 | 28.7 |
| Selectivity, %w | | | | | | |
| Ethylbenzene | 86.5 | 86 | 87 | 85.5 | 85.5 | 86 |
| Butylbenzene | 1.3 | 1.2 | 1.2 | 1.2 | 1.2 | 1.2 |
| Diethylbenzene | 10 | 10 | 9.5 | 10.5 | 10.5 | 10 |
| Triethylbenzene | 2 | 2.2 | 1.9 | 2.1 | 2.1 | 2.1 |
| Tetraethylbenzene | 0.6 | 0.5 | 0.5 | 0.6 | 0.6 | 0.5 |

ILLUSTRATIVE EMBODIMENT IVc

In Illustrative Embodiment IVc, the support employed was Pechiney alumina having a pore volume of 0.55 ml/g, surface area of 60 m$^2$/g, and an effective pore diameter of 370 A. Catalyst to support ratio was about 2.8:100. About 10 grams of the supported catalyst was loaded in the reactor. Reaction condition included a 750 psig pressure and a WHSV of about 3.0. The results are presented below in Table 5c.

Table 5c

| Time, hours | 5 | 28.5 | 50 | 72 | 93 | 98 |
|---|---|---|---|---|---|---|
| Temperature, ° C | 190 | 195 | 200 | 205 | 205 | 210 |
| Ethylene Conversion | 73 | 89 | 99 | 100 | 73 | 55 |
| Ethylbenzene, %w in product | 21.2 | 25.7 | 28.7 | 29 | 21 | 16 |
| Selectivity, %w | | | | | | |
| Ethylbenzene | 88 | 87 | 85.5 | 85 | 87.5 | 88.5 |
| Butylbenzene | 1.1 | 1.1 | 1.2 | 1.2 | 1.0 | 1.1 |
| Diethylbenzene | 10 | 10 | 11 | 11 | 9.5 | 9.5 |
| Triethylbenzene | 1.3 | 1.5 | 1.8 | 2.1 | 1.6 | 1.1 |
| Tetraethylbenzene | 0.2 | 0.4 | 0.6 | 0.6 | 0.2 | — |

E. Disproportionation of Toluene

Recently, with the increase in the production of synthetic fibers, demand for benzene and xylene has increased. Therefore, the so-called disproportionation process for converting toluene to benzene and xylene has been examined for industrial applications. Most of these processes employ Friedel-Crafts catalysts. Other reported processes employ silica-alumina, alumina-boria, or crystalline zeolites as catalysts. See, e.g., U.S. Pat. No. 3,576,895 and U.S. Pat. No. 3,553,277.

However, most of these known catalysts exhibit only a low catalytic activity for the disproportionation reaction of toluene, and further, these catalysts have such shortcomings as a relative short catalyst life and problems with extreme carbon deposition on the catalyst.

In the present invention, a toluene-containing stream is contacted with a catalyst of the instant invention in the liquid phase and at a temperature of between about 150° C and 225° C. In a preferred embodiment, a hydrogen gas-containing stream is also employed in the reaction.

The toluene feed for the present invention is typically obtained as a refinery process stream from an extraction process. Accordingly, the stream typically contains some benzene and xylene in addition to the toluene. Toluene concentrations of greater than about 50% volume are preferred, however.

The process may be carried out either as a batch or continuous type of operation, although it is preferred to carry out the process continuously. It has generally been established that the more intimate the contact between the feedstock and the catalyst, the better the yield of desired product obtained. With this in mind, the present process, when operated as a batch operation, is characterized by the use of vigorous mechanical stirring or shaking of the reactant and catalyst.

When employing a continous process, the feedstocks may be contacted with the supported catalyst in any suitable reactor. In one embodiment, the supported catalyst is packed in a vertical, tubular reactor bed with inert supports, such as ceramic balls or silicon carbide, above and below the supported catalyst to prevent entrainment of the solid catalyst. In a further embodiment, the supported catalyst is mixed with an inert material, such as quartz, and loaded in the reactor so as to improve the fluid dynamics of the system. The flow of the reactant feed stream may be upflow or downflow, with an upflow arrangement being preferred to ensure a liquid phase reaction.

Reaction temperature is varied between about 150° C and 225° C. The reaction temperature must be kept below about 225° C due to the lack of stability of the catalyst at temperatures of over 250° C. A preferred temperature range is between about 175° C and 210° C.

In general, the pressure in the reaction zone is maintained to keep the toluene in liquid phase, and accordingly, will vary which the particular feestock employed and the reaction temperatures. Typical reaction zone pressure varies from about 10 psig to about 2,000 psig.

The weight hourly space velocity effectively measures the catalyst concentration employed, and hence, also measures the relative activity of the catalyst. Weight hourly space velocity (WHSV) is defined as the weight per hour of toluene feed divided by the weight of catalyst (not including support) employed. For a non-supported catalyst, the WHSV varies between about 0.05 hr$^{-1}$ to about 1.0 hr$^{-1}$. For a supported catalyst, the WHSV varies from between about 0.5 hr$^{-1}$ to about 10.0 hr$^{-1}$. The larger WHSV employed for supported catalysts is possible because of the greater activity of the supported catalysts.

In a preferred embodiment, a gas stream is introduced into the reaction zone along with the toluene feed stream. Typically, the gas is an inert gas much as nitrogen. However, it has been found that when the gas stream also contains some hydrogen, the conversion of toluene is increased while the production of unwanted products such as $C_3$-$C_5$ cracked gases and non-volatile aromatic products is decreased. A preferred gas composition contains between about 2% to 95% hydrogen with the remainder being an inert gas such as nitrogen. The volume ratio of gas to toluene varies from about 0.5:1 to about 20:1.

The invention is further illustrated by means of the following Comparative Example and Illustrative Embodiments which are given for the purpose of illustration only, and the invention is not to be regarded as limited to any of the specific materials or conditions recited therein.

In the Comparative Example and Illustrative Embodiments, the reactor employed was a 17-inch stainless steel tube equipped with both a liquid feed upflow inlet and a nitrogen inlet. The catalyst bed occupied about 10 inches in the center of the reactor; and on either side of the catalyst bed were packed about 10 grams of carborumdum chips.

In all cases, the reactants were introduced in an upflow manner, pressure was kept at 300 psig to maintain a liquid phase, and the feed stream was 100% toluene. Catalyst concentration is measured by weight hourly space velocity (WHSV, hr$^{-1}$) which is defined as the weight of the toluene feed divided by the weight of catalyst (excluding support).

COMPARATIVE EXAMPLE Id

The catalyst employed in Comparative Example Id was prepared by grinding Nafion XR granules with a blender to 150 micrometer or less particle size. The ground material was then treated twice with 30% sulfuric acid to convert the material from a potassium (K$^+$) form to the H$^+$ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

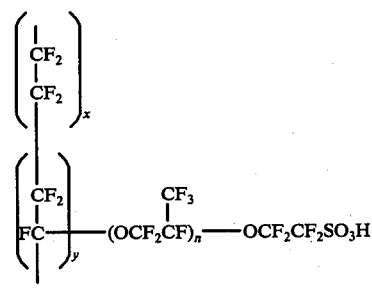

VI

In Comparative Example Id, the catalyst bed comprised 5 grams of the catalyst plus 5 grams of quartz particles. A stream of 100% nitrogen in a volume ratio of 1:1 with the toluene feed was maintained. The WHSV was maintained at 0.43 hr$^{-1}$. The results are presented below in Table 1d.

Table 1d

| Time, hr | 5 | 26 | 46.5 | 68.5 | 72.5 | 91.5 |
|---|---|---|---|---|---|---|
| Temperature, °C | 200 | 200 | 200 | 200 | 225 | 225 |
| Composition of Product %w | | | | | | |

Table 1d-continued

| Time, hr | 5 | 26 | 46.5 | 68.5 | 72.5 | 91.5 |
|---|---|---|---|---|---|---|
| $C_3-C_5$ | 0.8 | 0.8 | 0.8 | 0.8 | 1.0 | 0.4 |
| Toluene | 78 | 78.5 | 79 | 84 | 84 | 90 |
| Benzene | 9.9 | 9.9 | 9.5 | 7.3 | 7.3 | 4.6 |
| o-Xylene | 2.2 | 2.0 | 1.9 | 1.5 | 1.4 | 1.0 |
| p-Xylene | 2.6 | 2.4 | 2.3 | 1.8 | 1.8 | 3.7 |
| m-Xylene | 5.8 | 5.5 | 5.4 | 4.0 | 4.0 | |
| Trimethylbenzenes | 0.5 | 0.5 | 0.5 | 0.4 | 0.3 | 0.3 |
| Non-Volatile Aromatics | 0.5 | 0.5 | 0.5 | 0.5 | 0.5 | 0.4 |

ILLUSTRATIVE EMBODIMENT Id

In the Illustrative Embodiments Id and IId, the catalyst was prepared by impregnating a silica support with an ethanol solution of Nafion XR granules, and then removing the ethanol from the solid on a rotary evaporator leaving a 6% catalyst on support composition. The support was a high surface area silica having a 1.65 ml/g pore volume, 300 m²/g surface area and a 210 A average pore diameter. Ten grams of the resulting catalyst were loaded in the reactor. A stream of 100% hydrogen in a volume ratio of 2:1 with the toluene feed was maintained. The WHSV was kept at 3.6. The results are presented below in Table 2d.

Table 2d

| Time, hour | 3 | 6 | 22 | 25 | 28 | 30 |
|---|---|---|---|---|---|---|
| Temperature, °C | 200 | 200 | 200 | 200 | 200 | 225 |
| Composition of Product, %w | | | | | | |
| $C_3-C_5$ | 0.1 | 0.1 | 0.1 | 0.1 | 0.1 | 0.2 |
| Toluene | 86.5 | 87 | 87.5 | 87.5 | 87.5 | 81 |
| Benzene | 6.4 | 6.3 | 6.0 | 6.0 | 6.0 | 9.3 |
| o-Xylene | 1.3 | 1.2 | 1.2 | 1.1 | 1.1 | 1.9 |
| p-Xylene + m-Xylene | 5.4 | 5.2 | 5.2 | 5.2 | 5.0 | 7.3 |
| Trimethylbenzenes | 0.3 | 0.3 | 0.3 | 0.3 | 0.3 | 0.4 |
| Non-Volatile Aromatics | 0.05 | 0.05 | 0.05 | 0.05 | 0.05 | 0.1 |

ILLUSTRATIVE EMBODIMENT IId

This Embodiment was conducted in a similar manner to Illustrative Embodiment Id except that the gas stream employed comprised 6% volume hydrogen and 94% volume nitrogen. The results are presented below in Table 3d.

Table 3d

| Time, hour | 4 | 25 | 46 | 68 | 76 | 96 |
|---|---|---|---|---|---|---|
| Temperature, °C | 200 | 200 | 200 | 200 | 225 | 225 |
| Composition of product, %w | | | | | | |
| $C_3-C_5$ | 0.2 | 0.2 | 0.2 | 0.2 | 0.4 | 0.3 |
| Toluene | 79 | 79 | 80 | 81 | 72.5 | 90 |
| Benzene | 10 | 10.0 | 9.8 | 9.3 | 13.2 | 4.6 |
| o-Xylene | 2.1 | 2.1 | 2.0 | 1.9 | 2.7 | 1.0 |
| p-Xylene | 2.6 | 2.6 | 2.5 | 2.3 | 3.3 | 3.7 |
| m-Xylene | 5.7 | 5.5 | 5.3 | 5.0 | 7.1 | |
| Trimethylbenzenes | 0.4 | 0.5 | 0.4 | 0.4 | 0.6 | 0.2 |
| Non-Volatile Aromatics | 0.1 | 0.1 | 0.1 | 0.1 | 0.1 | — |

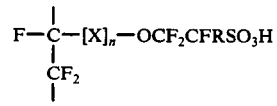

a)

or

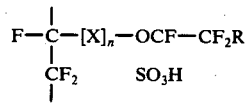

b)

where $n$ is 0, 1 or 2; R is a radical selected from the group consisting of fluorine and perfluorealkyl radicals having from 1 to 10 carbon atoms; and X is selected from the group consisting of:

$[O(CF_2)_m]$, $[OCF_2CFY]$ or $[OCFYCF_2]$ where $m$ is an integer from 2 to 10 and Y is a radical selected from the class consisting of fluorine and trifluoromethyl radical.

What is claimed is:

1. A liquid phase process for the preparation of ethylbenzene which conprises contacting an ethylene feed stream with a benzene feed stream at a reaction temperature of between about 125° C and about 225° C in the presence of a catalyst composition comprising a solid perfluorinated polymer catalyst supported on an inert porous carrier having an average pore diameter of between about 50 A and about 600 A in a weight ratio of catalyst to support of between about 0.1:100 and about 20:100 wherein said catalyst contains a repeating structure selected from the group of:

2. A process accroding to claim 1 wherein the mole ratio of said benzene stream to said ethylene stream varies from about 1.5:1 to about 10:1.

3. A process according to claim 1 wherein the weight hourly space velocity, defined as the weight per hour of the reactants divided by the weight of catalyst (including support) employed, varies from between about 0.5 to about 20.0 hr$^{-1}$.

4. A process according to claim 1 wherein said carrier is selected from the group consisting of alumina, silica, silica-alumina and porous glass.
5. A process according to claim 4 wherein said carrier is silica.
6. A process according to claim 1 wherein said catalyst has the general structure
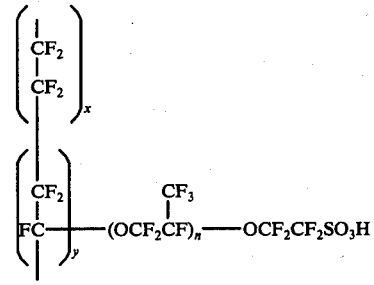
VI
where $n$ equals 1 or 2 and the ratio of $x$ over $y$ varies from about 2 to about 50.
* * * * *